US00PP29966P2

(12) United States Plant Patent
Larse

(10) Patent No.: US PP29,966 P2
(45) Date of Patent: Dec. 11, 2018

(54) STRAWBERRY PLANT NAMED 'PREAKNESS'

(50) Latin Name: ***Fragaria* x *ananassa***
Varietal Denomination: Preakness (a.k.a 108965)

(71) Applicant: Sweet Darling Sales, Inc., Aptos, CA (US)

(72) Inventor: John Larse, Watsonville, CA (US)

(73) Assignee: Sweet Darling Sales, Inc., Aptos, CA (US)

( * ) Notice: Subject to any disclaimer, the term of this patent is extended or adjusted under 35 U.S.C. 154(b) by 0 days.

(21) Appl. No.: 15/731,553

(22) Filed: Jun. 28, 2017

Related U.S. Application Data

(60) Provisional application No. 62/355,575, filed on Jun. 28, 2016.

(51) Int. Cl.
*A01H 5/08* (2018.01)

(52) U.S. Cl.
USPC ..... Plt./209

(58) Field of Classification Search
USPC ..... Plt./209, 208
See application file for complete search history.

*Primary Examiner* — Annette H Para
(74) *Attorney, Agent, or Firm* — Cooley LLP

(57) ABSTRACT

The present invention provides a new and distinct strawberry variety designated as 'Preakness' (a.k.a. '108965').

3 Drawing Sheets

Latin name of the genus and species: *Fragaria* x *ananassa.*

Varietal denominations: 'Preakness' (a.k.a. '108965').

BACKGROUND OF THE INVENTION

The present invention relates to a new and distinct strawberry plant designated as 'Preakness' (a.k.a. '108965'). 'Preakness' is a day neutral strawberry plant.

'Preakness' (a.k.a. '108965') is the result of a controlled-cross between a female parent cultivar designated '106734' (unpatented, proprietary cultivar) and a male parent cultivar designated '108296' (unpatented, proprietary cultivar) made by the Inventor and was first fruited in Watsonville, Calif. growing fields. Following selection and during testing, the plant was originally designated '108965' and subsequently named 'Preakness'.

These new varieties were asexually reproduced via runners (stolons) by the inventor at Watsonville, Calif. Asexual propagules from the original source have been tested in Watsonville growing fields and to a limited extent, grower fields in high elevation. The properties of these varieties were found to be transmissible by such asexual reproduction. These cultivars are stable and reproduce true to type in successive generations of asexual reproduction.

BRIEF SUMMARY OF THE INVENTION

This invention relates to a new and distinctive strawberry plant designated as 'Preakness'. This strawberry plant is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months. 'Preakness' presents strong ease of harvest qualities including good visibility though petiole canopy of fruiting plants, and a good flower stem length to petiole length ratio. The plant presents a semi-upright growth habit and a round to oblate plant shape, and produces mostly conic fruit and globose conic fruit. The mid-April through mid-September yield of 'Preakness' is high and the cull rate is low.

The following traits and photographs in combination distinguish strawberry plant 'Preakness' from known strawberry varieties. In addition, each of these new cultivars was confirmed to be a unique strawberry germplasm when tested against the California Seed & Plant Lab, Inc. (Elverta, Calif.) database using Short Sequence Repeats (SSRs). Plants for the botanical measurements in the present application were grown as annuals. Any color references are made to The Royal Horticultural Society Colour Chart, 1995 Edition, except where general terms of ordinary dictionary significance are used. The fruit produced by each new cultivar is attractive and of excellent quality.

DESCRIPTION OF THE DRAWINGS

The accompanying color photographs depict various characteristics of the cultivar as nearly true as possible to make color reproductions.

DETAILED DESCRIPTION OF THE INVENTION

'Preakness' (a.k.a. '108965')

Figure 1:
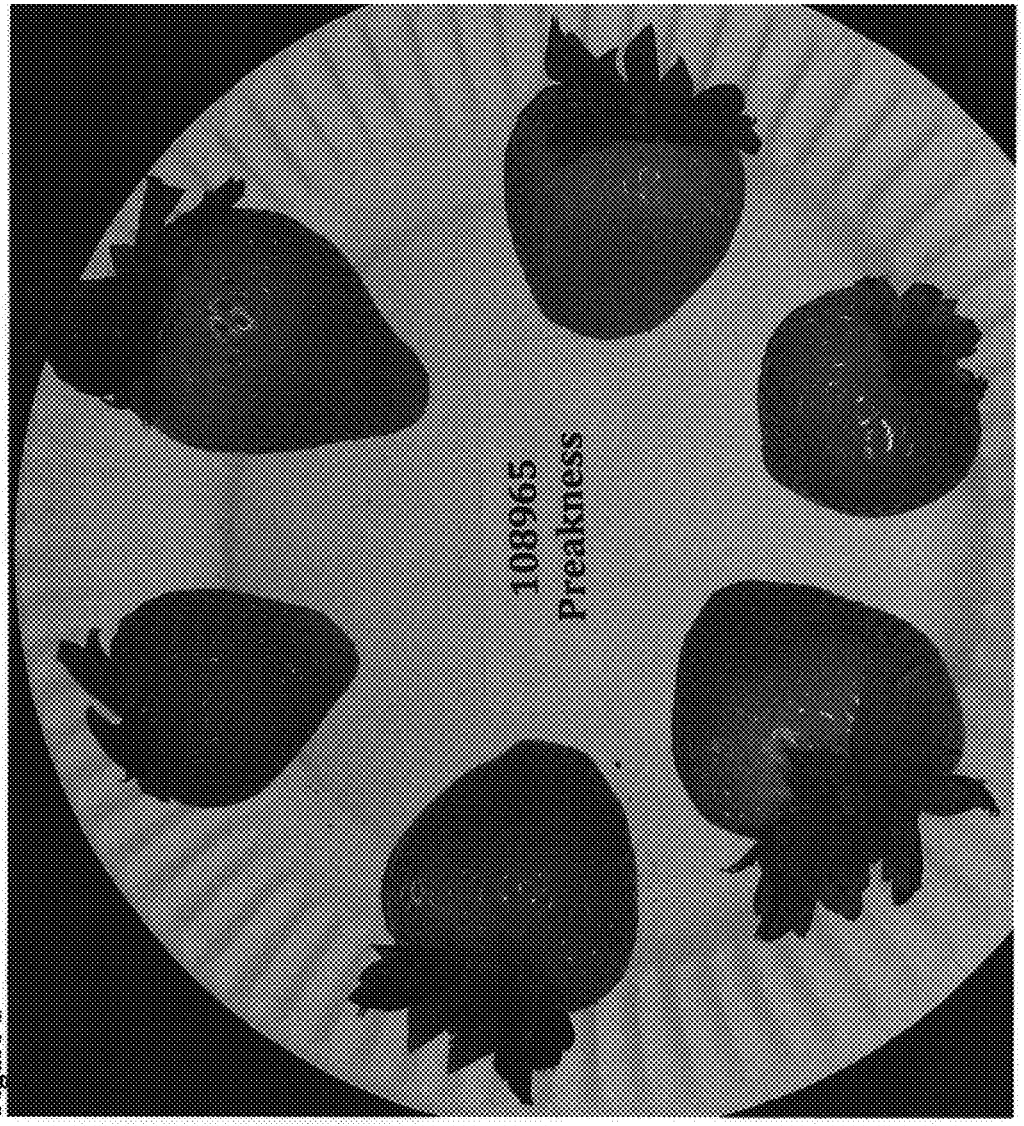
FIG. 1 shows fruits of 'Preakness'.
Figure 2:
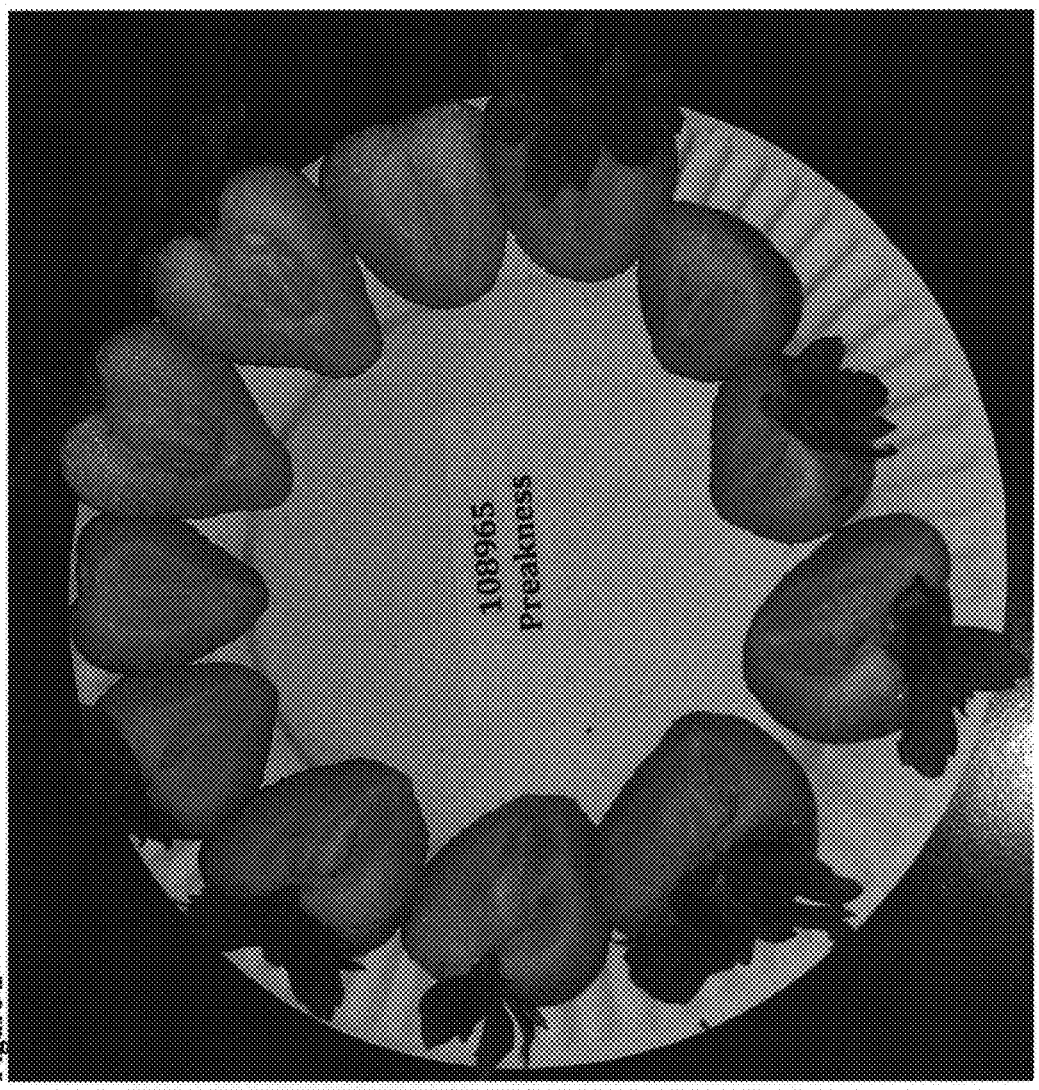
FIG. 2 shows sliced fruits of 'Preakness'.
Figure 3:
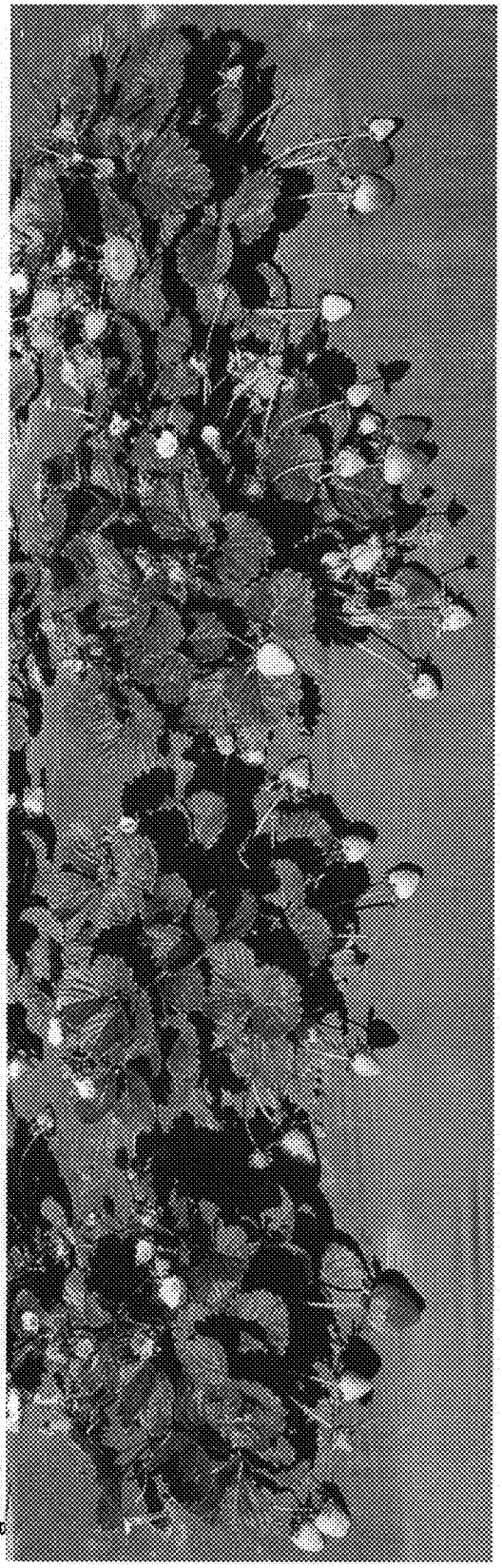
FIG. 3 shows 'Preakness' plants.

This invention relates to a new and distinctive day-neutral type strawberry cultivar designated as 'Preakness'. It is primarily adapted to the climate and growing conditions of the central coast of California. This region provides the necessary temperatures required for it to produce a strong vigorous plant and to remain in fruit production from March through October. The nearby Pacific Ocean provides the needed humidity and moderate day temperatures and evening chilling to maintain fruit quality for the production months.

The following traits in combination distinguish strawberry variety 'Preakness' from the known strawberry varieties. Plants for the botanical measurements in the present application were grown as annuals. In the following description, color references are made to The Royal Horticultural Society Colour Chart, 1995 Edition, except where general terms of ordinary dictionary significance are used.

The detailed botanical description in Table 1 was observed when the plants were 33 weeks after planting.

'Preakness' has not been observed under all possible environmental conditions, and the phenotype may vary significantly with variations in environment. The following observations, measurements, and comparisons describe this plant as grown under normal conditions in Watsonville, Calif. unless otherwise noted.

TABLE 1

| Preakness | | |
|---|---|---|
| CharType | Characteristic | Preakness |
| General | Plant Habit | annual |
| | Plant Growth Habit | semi-upright |
| | Plant Height | 26 cm |
| | Plant Width | 30 cm |
| | Plant Width-Crown | 5 cm |
| | Density of foliage, vigor | light |
| | Plant vigor | moderate |
| Leaf | Terminal leaflet width (mm) | 75 |
| | Terminal leaflet length (mm) | 75 |
| | No. teeth/terminal leaflet: | 14 to 18 |
| | Shape of the terminal leaflet base | obtuse |
| | Shape of terminal leaflet in cross-section | concave |
| | Margin description of the terminal | serrate to crenate |
| | Color of upper side of leaves | 137A |
| | Color of lower side of leaves | 139C |
| | Leaf blistering | weak |
| | Leaf glossiness | medium |
| Limbs | Petiole length (cm) | 10.5 |
| | Petiole diameter (mm) | 3.89 |
| | Petiole color | 145A |
| | Petiolule length (mm) | 19 |
| | Petiolule diameter (mm) | 3.89 |
| | Attitude of hairs on petiole and pedicel | upwards |
| | Stipule pubescence | medium |
| | Stipule length (cm) | 2.6 |
| | Stipule size | small |
| | Stipule width (cm) | 0.7 |
| | Stipule anthocyanin | absent |
| | Stipule color (color code) | 145A |
| | Pedicel color (color code) | 145A |
| | Peduncle length (cm) | 20.5 |
| | Peduncle size | medium |
| | Peduncle attitude | semi erect |
| | Peduncle pubescence, attitude of hairs | medium, upwards |
| Inflorescence | Inflorescence position relative to foliage | even to above |
| | Flower arrangement of petals | overlapping |
| | Petal length (cm) | 1.4 |
| | Petal width (cm) | 1.2 |
| | Petal number per flower | 5 to 6 |
| | Upper Petal color | 155B |
| | Lower Petal color | 155C |
| | Calyx diameter (cm) | 3.2 |
| | Corolla diameter (cm) | 2.4 |
| | Sepal length (cm) | 1.6 |
| | Sepal width (cm) | 0.3 |
| | Time of flowering (50% of plants in bloom) | March |
| | Shape of stigma | capitate |

TABLE 1-continued

| Preakness | | |
|---|---|---|
| CharType | Characteristic | Preakness |
| | Color of stigma | 4A |
| | Length of style (mm) | 2 |
| | Color of style | 4A |
| | Color of the ovary | 145B |
| | Length of the stamens (mm) | 4 |
| | Number of stamen | 22 |
| | Anther color | 20A |
| | Shape of anther | dorsifixed |
| | Size of anther | small to medium |
| | Amount of pollen | moderate |
| | Color of pollen | 15B |
| | Color of filament | 145C |
| | Length of filament (mm) | 3 |
| | Number of flowers per truss | 3 to 7 |
| Stolon | Stolon number | 3 |
| | Stolon anthocyanin | 183A |
| | Widest diameter of stolon At leaf attachment (mm) | 3.82 |
| | Stolon color | 145A |
| Fruit | Number of fruit per truss | 2 to 5 |
| | Fruit length (cm) | 5.2 |
| | Fruit width (cm) | 4.7 |
| | Fruit skin color | 45A |
| | Fruit flesh color excluding core | 44A |
| | Fruit core length (cm) | 2.9 |
| | Fruit core width (cm) | 1.7 |
| | Fruit core color | 37A |
| | Fruit weight (g) | 26.3 |
| | Predominant fruit shape | conic to short wedge |
| | Shape difference between primary & secondary fruits | Similar shape |
| | Width of band without of achenes | medium |
| | Fruit glossiness | medium to strong |
| | Position of achenes | below surface |
| | Achene color | 145A |
| | Achenes per fruit | 220 |
| | Achene weight (g) | 0.1 |
| | Position of calyx | inserted |
| | level of adherence of calyx | strong |
| | Color of calyx | 137A |
| | Firmness of flesh | medium to firm |
| | Evenness of flesh color | nearly even |
| | Sweetness (brix) | 6 |
| | pH | 3.42 |
| | Yield (g per plant per season) | 2817 |

When 'Preakness' is compared to the proprietary female parent (106734), 'Preakness' presents its florescence as a spray of flowers from a relatively small roundish plant. However, the female parent is a large cylindrically shaped tower-like plant with a uniformly distributed presentation of large bright white florescence that protrudes from canopy as though from all areas of the plant and at different levels appearing to be topiary-like. 'Preakness' flowers are much less visible from a distance of 100 feet away whereas flowers of the female parent are prominently visible in a mass-planting large test block. 'Preakness' also differs from its female parent because many of the fruits of the female parent have a single long crease that appears to divide the fruit into two parts, and have a long flattened conic shape. Furthermore, the fruit of the female parent is conic and long conic but with variance between orthogonal mid-line latitude dimensions that accounts for the Spanish language planchada descriptor, as in flattened. Compared to the female parent, the plant shape of 'Preakness' has a semi-upright plant growth habit and is oblate to round in shape. The female parent presents an upright plant growth habit and has a large cylindrically shaped tower-like fruiting plant.

The cull rate of fruiting plants of 'Preakness' is slightly lower than the cull rate of the female parent.

When 'Preakness' is compared to the proprietary male parent (108296), fruits of the male parent are primarily long conic and conic in shape while fruits of 'Preakness' are conic and globose conic in shape. Fruits produced by 'Preakness' are significantly larger than fruits produced by the male parent.

When 'Preakness' is compared to the check variety 'Monterey' (U.S. Plant Pat. No. 19,767), 'Preakness' differs from 'Monterey' in plant size and shape. 'Monterey' is larger and taller with more cylindrical shape than 'Preakness' having a small plant size and a round plant shape. Additionally, fruiting plants of 'Preakness' are higher than fruiting plants of 'Monterey' when comparing a flower stem length to petiole length ratio. 'Preakness' plants are slightly less susceptible to powdery mildew than 'Monterey' plants. Fruits produced by 'Preakness' are smaller than fruits produced by 'Monterey'.

TABLE 2

Comparison of fruit features between 'Preakness' and the proprietary female parent

| HYBRID ID | HYBRID NAME | FRUIT WIDTH (mm) | FRUIT HEIGHT (mm) |
|---|---|---|---|
| 106734 | Female Parent | 40.83 | 49.96 |
| 108965 | Preakness | 40.47 | 45.27 |

| HYBRID ID | FRUIT RATIO (Height/ Width) | FRUIT SHAPE* | HARD-NESS (newtons) | Yield (g/clone) |
|---|---|---|---|---|
| 106734 | 1.22 | 7 | 7.78 | 1771 |
| 108965 | 1.12 | 6 | 7.62 | 943 |

*Fruit shape: 1. Oblate; 2. Globose; 3. Fan Lobes; 4. Necked; 5. Short wedge; 6. Symmetric conic; 7. Conic; 8.Long conic; 9. Long wedge

TABLE 3

Comparison of fruit features between 'Preakness' and the check variety

| HYBRID ID | HYBRID NAME | FRUIT WIDTH (mm) | FRUIT HEIGHT (mm) |
|---|---|---|---|
| Check Variety | Monterey (U.S. Plant Pat. No. 19,767) | 43.70 | 48.33 |
| 108965 | Preakness | 40.47 | 45.27 |

| HYBRID ID | FRUIT RATIO (Height/ Width) | FRUIT SHAPE* | HARD-NESS (newtons) | Yield (g/clone) |
|---|---|---|---|---|
| Check Variety | 1.11 | 6 | 9.04 | 840 |
| 108965 | 1.12 | 6 | 7.62 | 943 |

*Fruit shape: 1. Oblate; 2. Globose; 3. Fan Lobes; 4. Necked; 5. Short wedge; 6. Symmetric conic; 7. Conic; 8. Long conic; 9. Long wedge

The invention claimed is:

1. A new and distinct cultivar of strawberry plant named 'Preakness' substantially as shown and described herein.

* * * * *